United States Patent
Braun et al.

(10) Patent No.: US 9,200,935 B2
(45) Date of Patent: Dec. 1, 2015

(54) HIGH-PRECISION DETERMINATION OF THE MASS PROPORTION OF A COMPONENT IN A MULTI-COMPONENT FLUID

(75) Inventors: Gilbert Braun, Herzogenrath (DE); Peter Kury, Essen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 96 days.

(21) Appl. No.: 14/237,875

(22) PCT Filed: Aug. 22, 2012

(86) PCT No.: PCT/EP2012/066328
§ 371 (c)(1),
(2), (4) Date: Feb. 8, 2014

(87) PCT Pub. No.: WO2013/026871
PCT Pub. Date: Feb. 28, 2013

(65) Prior Publication Data
US 2014/0190271 A1 Jul. 10, 2014

(30) Foreign Application Priority Data
Aug. 23, 2011 (EP) .................................. 11178490

(51) Int. Cl.
*G01F 1/74* (2006.01)
*G01N 33/00* (2006.01)
*G01F 15/08* (2006.01)

(52) U.S. Cl.
CPC *G01F 1/74* (2013.01); *G01F 15/08* (2013.01); *G01N 33/0014* (2013.01)

(58) Field of Classification Search
CPC ............... G01F 1/74; G01F 1/44; G01F 1/00; G01F 7/00; E21B 47/10
USPC ............ 73/861.04, 197, 861.63, 155, 152.31; 702/45
See application file for complete search history.

(56) References Cited

U.S. PATENT DOCUMENTS

| | | | |
|---|---|---|---|
| 4,441,362 A * | 4/1984 | Carlson | 73/152.31 |
| 5,050,109 A | 9/1991 | Ladd | |
| 5,589,642 A * | 12/1996 | Agar et al. | 73/861.04 |
| 6,318,156 B1 | 11/2001 | Dutton et al. | |

(Continued)

FOREIGN PATENT DOCUMENTS

| CA | 2389145 C | 2/2007 |
|---|---|---|
| CN | 1074145 C | 10/2001 |
| CN | 1343864 A | 4/2002 |
| CN | 1285512 C | 11/2006 |
| CN | 101496959 A | 8/2009 |

(Continued)

*Primary Examiner* — Jewel V Thompson
(74) *Attorney, Agent, or Firm* — Beusse Wolter Sanks & Maire

(57) ABSTRACT

A method to determine a mass proportion of a first component of a multi-component fluid is provided that includes separating the first component in a separation step at least in part from the multi-component fluid, determining at least two reference flow rates, selected from a flow rate of the multi-component fluid supplied to the separation step, a flow rate of a residual fluid resulting from the separation of the first component, and a flow rate of a separation fluid accumulating in the separation step, and determining the mass proportion of the first component from the selected reference flow rates, taking into account a non-separated residual content of the first component in the residual fluid. An extraneous content of an additional separated component of the multi-component fluid is additionally taken into account.

9 Claims, 2 Drawing Sheets

(56) References Cited

U.S. PATENT DOCUMENTS

| | | | |
|---|---|---|---|
| 6,422,092 B1 * | 7/2002 | Morrison et al. | 73/861.04 |
| 7,054,764 B2 * | 5/2006 | Williams et al. | 702/45 |
| 7,389,687 B2 * | 6/2008 | Gysling et al. | 73/200 |
| 2003/0136185 A1 | 7/2003 | Dutton | |

FOREIGN PATENT DOCUMENTS

| | | |
|---|---|---|
| DE | 4433451 A1 | 3/1996 |
| JP | H08101111 A | 4/1996 |
| JP | H11326310 A | 11/1999 |
| JP | 2003513234 A | 4/2003 |

* cited by examiner

HIGH-PRECISION DETERMINATION OF THE MASS PROPORTION OF A COMPONENT IN A MULTI-COMPONENT FLUID

CROSS REFERENCE TO RELATED APPLICATIONS

This application is the US National Stage of International Application No. PCT/EP2012/066328 filed Aug. 22, 2012, and claims the benefit thereof. The International Application claims the benefit of European Application No EP11178490 filed Aug. 23, 2011. All of the applications are incorporated by reference herein in their entirety.

FIELD OF INVENTION

The invention relates to a method for determining a mass proportion of a component of a multi-component fluid.

BACKGROUND OF INVENTION

The term "fluid" relates generally to a gas, a liquid or a flowable phase mixture consisting of gaseous, liquid and/or solid constituents. The term "component" refers here generally to a separable proportion of the multi-component fluid with specific chemical and/or physical properties, on the basis of which this component can be distinguished from at least one further component of the multi-component fluid. The components of the multi-component fluid are formed here in particular by different chemical substances. In principle, a component of the multi-component fluid may however also already be formed itself from a mixture of different chemical substances. Similarly, different phases (states of aggregation) of the same chemical substance or of the same chemical substance mixture may form different components of the multi-component fluid. That component of which the mass proportion is to be determined according to the method is also referred to hereinafter—to distinguish terminologically from further components of the multi-component fluid—as the "first component".

The multi-component fluid is in particular a synthesis gas, as is used for example as a fuel gas for combustion in power plant gas turbines. Such a synthesis gas usually consists of hydrogen ($H_2$), carbon monoxide (CO), carbon dioxide ($CO_2$), nitrogen ($N_2$) and water ($H_2O$). The water content is usually varied, for example by means of mixing in steam, in order to set the reactivity of the combustion gas such that required emission limits (for example with regard to the nitrous oxide ($NO_x$) output) are maintained. The water content of a typical synthesis gas may reach or exceed 50%.

In the combustion of a synthesis gas in a power plant gas turbine, a real-time gas analysis is desirable, since the gas composition, and consequently the variables that are important for the combustion in the gas turbine (for example the Wobbe index and the reactivity), are subject to variations over time that are due to the gasification process and are caused for example by changing process conditions or starting materials.

On account of the high combustion gas temperatures in the range of approximately 200° Celsius and the high proportion of water of customary synthesis gases, commonly used methods for gas analysis, in particular infrared absorption measurement and gas chromatography, cannot be applied directly to the combustion gas. Rather, before such a gas analysis is applied, generally a drying and cooling of the combustion gas is required. However, this cooling and drying process already leads disadvantageously to a considerable falsification of the original gas composition, especially since a considerable part of the water originally contained in the synthesis gas is removed.

DE 44 33 451 A1 discloses a method for determining the water content in a gas in which the volumetric flow or mass flow of the gas to be analyzed is determined by measuring the differential pressure falling across a flow resistance. Following this measurement, the water contained in the gas is removed at least for the most part in a separation step by condensation. After the separation step, the mass flow or volumetric flow of the dried gas resulting from the separation step is determined. This measurement in turn takes place indirectly by way of the differential pressure falling across a flow resistance. The mass proportion of the water originally contained in the gas is deduced here from the difference in the measured mass flow or volumetric flows. The residual moisture of the dried gas is taken into account here as a correction factor. The dried and cooled gas can be subsequently fed to a gas analysis system.

U.S. Pat. No. 5,050,109 A also discloses a method and a device for determining the humidity of ambient air surrounding an aircraft in flight. In this method, moisture is separated from a captured flow of ambient air in a water separator. The respective mass flow, at least of the flow of air fed to the water separator and of the moisture discharged from the water separator, are measured. The humidity of the ambient air is calculated from the measured mass flow values, while additionally taking into account the efficiency of the water separator.

Finally, US 2003/0136185 A1 discloses a method and a device for determining the volumetric flow rate in a three-phase mixture of water, oil and gas. In this method, a predominantly gaseous component and a predominantly liquid component are separated from the three-phase mixture in a separator, the predominantly liquid component containing a proportion of water and a proportion of oil. The density of the predominantly liquid component is determined by means of a Coriolis flowmeter. Furthermore, the relative proportion of water of the predominantly liquid component is determined by means of a hydrometer. The density and the relative proportion of water of the predominantly liquid component are in this case determined at a point in time at which the predominantly liquid component is substantially free of entrained gas.

SUMMARY OF INVENTION

An object herein is to provide a method for determining the mass proportion of a component of a multi-component fluid that can be easily implemented but at the same time has a high degree of precision. The method is intended at the same time to make possible in particular a high-precision determination of the proportion of water of a synthesis gas under the conditions usually prevailing in a power plant gas turbine. A further object herein is to provide a device that is particularly suitable for carrying out the method.

In the case of the method, for determining a mass proportion of a first component of a multi-component fluid of the type defined at the beginning, the first component is at least partially separated from the multi-component fluid in a separation step. For terminological distinction, in the following only the fluid that is fed to the separation step and still contains the first component in the full mass proportion to be determined is referred to as the "multi-component fluid". By contrast, the fluid resulting from the separation step, with complete or partial removal of the first component, is referred to hereinafter as the "residual fluid". The fluid occurring in the course of the separation step and containing the separated first component is referred to hereinafter as the "separation fluid".

Not only the multi-component fluid (fed to the separation step) but also the residual fluid (resulting from the separation step) and the separation fluid (occurring in the separation step) are respectively assigned a flow rate, which can in each case be given for example in units of mass flow or volumetric flow. In the course of the method according to the invention, at least two of these three flow rates are determined as reference flow rates. In an evaluation step of the method, the mass proportion of the first component is determined from these reference flow rates.

In order to avoid a falsification of the calculated mass proportion when there is a non-ideal separation of the first component, account is taken in the calculation of this mass proportion on the one hand of a (non-separated) residual proportion of the first component in the residual fluid. According to the invention, account is additionally taken in the calculation of the mass proportion of the first component of a proportion of at least one further component that is separated at the same time in the separation step, and is consequently contained in the separation fluid as an "extraneous proportion".

The multi-component fluid is in particular a synthesis gas of the type described above. The first component, the mass proportion of which is to be determined according to the method, is particularly water. In this application case, according to the method account is taken in particular of the proportion of the carbon dioxide that is always separated to a certain extent at the same time along with the water as an extraneous proportion. In principle, however, the method according to the invention may also be applied to other multi-component fluids, for example to the determination of the mass proportion of sand (as the first component) in a water-sand mixture. In this application case, according to the method, the proportion of the water separated together with the sand is taken into account as an extraneous proportion.

To achieve a particularly high degree of measuring precision, the reference flow rates included in the calculation are preferably not determined indirectly, but by direct measurement of the mass flow of the multi-component fluid, of the residual fluid and of the separation fluid. For the direct mass flow measurement, a Coriolis mass flowmeter is preferably used here in each case.

In an expedient embodiment of the method, the pressure of the multi-component fluid is controlled to a predetermined setpoint value, and is consequently kept constant—within the tolerance of the control. This measure is based on the finding that pressure fluctuations always lead to a disturbance of the balance of the flow rate or mass of the fluid flows entering the separation step or emerging from the separation step. In actual fact—unlike in the case of a steady state—during a pressure fluctuation the flow rates of the multi-component fluid, of the residual fluid and of the separation fluid often do not add up to zero, especially since the system of lines carrying these fluids has a—pressure-dependently varying—storage capacity. Thus, generally when there is rising pressure, an increasing amount of fluid is stored in the system of lines, which regularly has the effect that the flow rate of the multi-component fluid temporarily exceeds the sum of the flow rates of the separation fluid and the residual fluid. An opposite flow-rate difference occurs when there is falling fluid pressure. As is known, these effects sometimes lead to considerable errors in the determination of the mass proportion of the first component, which are avoided in a particularly easy and effective way by the pressure control.

A further improvement of the measuring precision is achieved in a preferred variant of the method by control-related pressure fluctuations (known as control oscillations) being eliminated or at least reduced by a damping element arranged downstream of the pressure controller. In a particularly simple and advantageous embodiment, a filter is used here as the damping element. In the application case of synthesis gases, a coarse-meshed gas filter, for example of sintered material or ceramic, with a pore size of between 200 and 500 µm, is used here in particular.

If the multi-component fluid is a gas flow, the separation of the first component preferably takes place by condensation in a condenser (also referred to as a gas cooler or cooling trap). The use of such a condenser is advisable in particular for the application of the method to a synthesis gas for a gas turbine, especially since the synthesis gas is at the same time cooled by the condenser to a temperature that is suitable for the further gas analysis.

The residual proportion of the first component in the residual fluid may in principle, within the scope of the invention, be determined by measurement or be estimated on the basis of empirical values. The former however often involves comparatively great effort, the latter often involves comparatively great imprecision. If the separation of the first component takes place by condensation, it has on the other hand been found that determining the residual proportion from the condensation curve of the first component is both easy to realize and precise. Here, the saturation vapor pressure of the first component (which can be read off from the condensation curve) at the temperature prevailing in the condenser (condenser temperature) is expediently used.

By contrast, the extraneous proportion of the further component in the separation fluid is preferably determined on the basis of the solubility of the further component in the first component. In this case, the value of the solubility at the condenser temperature is in turn expediently used.

In an expedient refinement of the method, the mass proportion of the first component is determined on the basis of the equation $$x_W = \frac{1}{1+\beta} + \left(1 - \frac{1}{1+\beta} - \frac{1}{1+\alpha}\right)\frac{M_2}{M_1}$$

In this equation $x_W$ stands for the mass proportion of the first component to be determined according to the method, $T_K$ stands for the condenser temperature, $\alpha=\alpha(T_K)$ stands for the mass density proportion of the first component in the residual gas corresponding to the saturation vapor pressure at the condenser temperature, $\beta=\beta(T_K)$ stands for the solubility of the further component in the first component at the condenser temperature, $M_1$ stands for the flow rate of the multi-component fluid fed to the separation step, chosen as the first reference flow rate, and $M_2$ stands for the flow rate of the residual fluid resulting from the separation step due to the separation of the first component, chosen as the second reference flow rate.

In an advantageous variant, the free gas volume in the condenser that is possibly used for the separation of the first component is kept constant by controlled withdrawal of the separation fluid from the condenser. Also by this method—in a way similar to the previously described pressure control—the storage capacity of the system of lines carrying the fluid is kept at least approximately constant, which has a positive effect on the achievable measuring precision.

In an expedient form, the device herein comprises a separation unit for the at least partial separation of the first component from the multi-component fluid. The device also comprises a first flow-rate measuring unit and a second flow-rate measuring unit for respectively measuring one of the at least two reference flow rates, these flow-rate measuring units preferably being Coriolis mass flowmeters.

The device herein finally comprises an evaluation unit, which is formed for performing the method described above in one of its variants. In actual fact, the evaluation unit is designed for determining the mass proportion of the first component from the reference flow rates, it taking into account both the non-separated residual portion of the first component in the residual fluid and the extraneous proportion of the further component that is separated at the same time in the separation fluid.

In a preferred form, the evaluation unit is in particular a computer, in which the instructions required for the method to be automatically carried out are implemented by software in the form of a control program.

To make the fluid pressure more uniform, and consequently improve the measuring precision, a pressure controller is preferably arranged upstream of the separation unit. To reduce control-related pressure fluctuations, a filter, in particular a filter of the type described above, is arranged between the pressure controller and the separation unit. When the device is applied to the analysis of gas flows, the separation unit is preferably formed as a condenser (also: a gas cooler or cooling trap). The condenser is preferably assigned here a filling level controller, which provides the effect—within predetermined control tolerances—of keeping the free gas volume in the condenser constant by controlled withdrawal of the separation fluid.

BRIEF DESCRIPTION OF THE DRAWINGS

Exemplary embodiments of the invention are explained in more detail below on the basis of a drawing, in which.

DETAILED DESCRIPTION OF INVENTION

Parts and variables that correspond to one another are always provided with the same designations in all of the figures.

Figure 1:
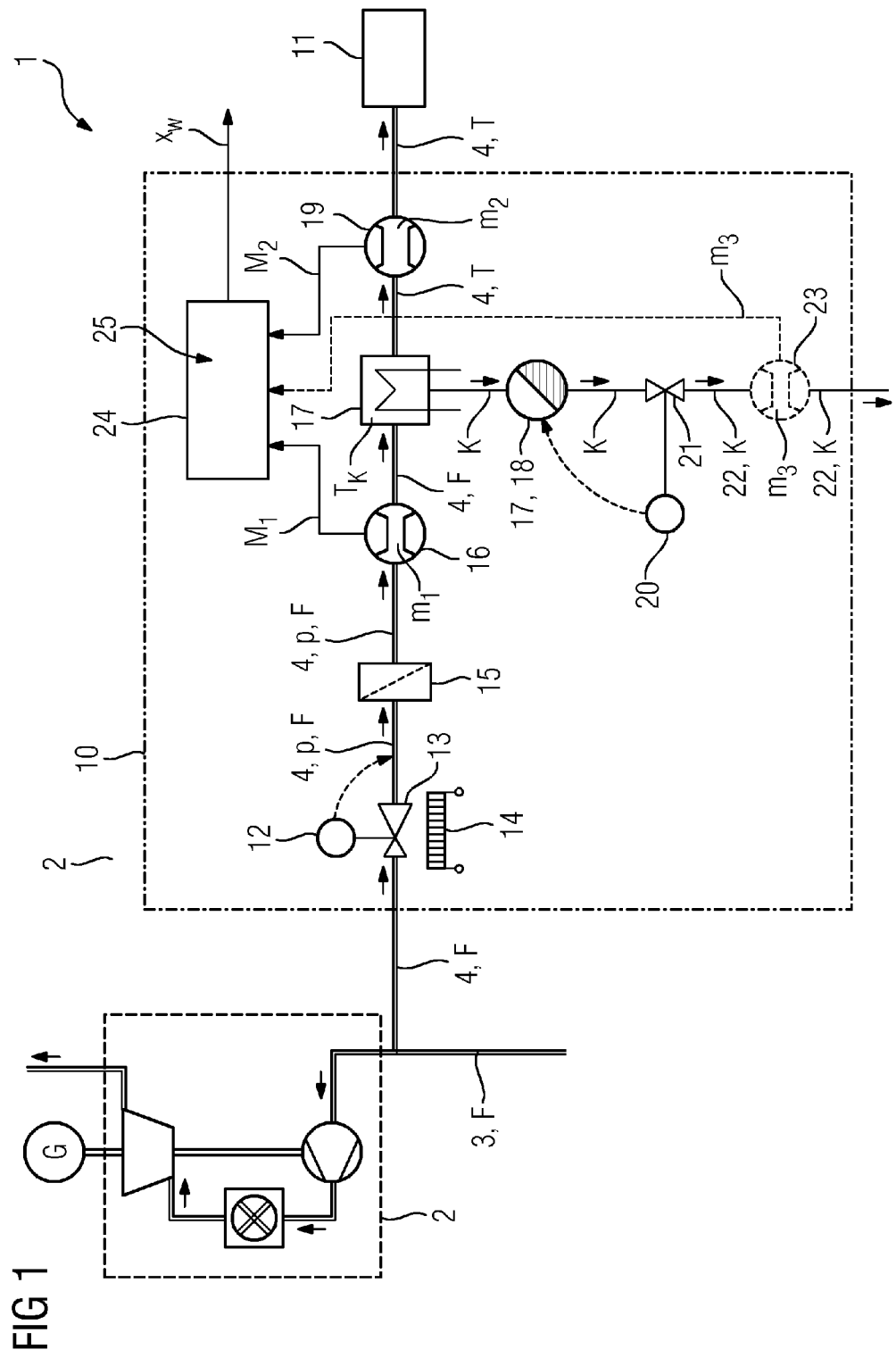
FIG. 1 shows in a roughly schematic simplified form a gas-turbine power plant with a gas turbine and a main gas line for feeding a synthesis gas to the gas turbine, and also a sample gas line, branching off from the main gas line, for the real-time analysis of the synthesis gas, a device for determining the mass proportion of the water contained in the synthesis gas being arranged in the sample gas line.

In FIG. 1, a (gas-turbine) power plant 1 is represented in a roughly schematic simplified form. The central component part of the power plant 1 is formed by at least one gas turbine 2, to which a compressed synthesis gas is fed by way of a (main) gas line 3 for combustion. This synthesis gas (with a high water content) is referred to hereinafter as wet gas F. The wet gas F is a multi-component fluid as defined above, which is composed of a number of gaseous components, specifically water ($H_2O$) and also carbon monoxide (CO), carbon dioxide ($CO_2$), hydrogen ($H_2$), nitrogen ($N_2$) and possibly traces of further substances. The wet gas F is produced here in particular in a gasification process, for example from biomass, coal, tar or asphalt, by rich (sub-stoichiometric) partial combustion with oxygen ("oxygen blown") or air ("air blown") and the addition of water.

The wet gas F has in particular a temperature of about 200° C., a pressure of about 35 bar. It has a (fluctuating) mass proportion of water, which is typically of the order of magnitude of approximately 50%.

In order to counteract fluctuations in the composition of the wet gas F, and consequently optimize the combustion, the wet gas F is analyzed in real time. For this purpose, branching off from the main gas line 3 is a sample gas line 4, by way of which a small part of the wet gas F is continuously removed. Arranged in the sample gas line 4 there is firstly a device 10, by means of which the mass proportion $x_W$ of the water W contained in the wet gas F is determined in the way according to the invention. The water W consequently forms the "first component" of the wet gas F as defined above. For reasons of simplification, no further differentiation is made below between the other components D of the wet gas F (that is in particular CO, $CO_2$, $N_2$ and $H_2$).

Arranged downstream of the device 10 within the sample gas line 4 is a gas analysis unit 11, which is for example a gas chromatograph. As an alternative to this, the gas analysis unit 11 may however also determine the gas composition by the use of resistive or capacitive sensors, by measurement of the thermal conductivity, the thermal conducting capacity and/or the refractive index, by measurement of the microwave and/or infrared absorption, by measurement of the Raman scattering or on the basis of some other commonly used method of gas analysis.

The device 10 comprises on the input side a pressure controller 12, in particular in the form of a customary membrane controller, which lowers the pressure of the wet gas F taken from the main gas line 3 to a pressure p corresponding to a predetermined setpoint value, for example approximately 2 bar, by controlling an assigned throttle valve 13. The throttle valve 13 is heated here by a heater 14, in order to be certain to eliminate the possibility of premature condensation of water W.

Minor pressure fluctuations on a rapid timescale (control oscillations) of the wet gas F, as are regularly caused by the pressure controller 12, are evened out by a damping element arranged downstream of the throttle valve 13 in the form of a coarse-meshed gas filter 15 with a pore size of for example approximately 350 µm.

Arranged downstream of the gas filter 15 is a first (Coriolis) mass flowmeter 16. This mass flowmeter 16 directly determines the mass flow $m_1$ of the wet gas F flowing within the sample gas line 4 as the first reference flow rate $M_1$:

$$M_1 := m_1 \qquad \text{Equation 1}$$

After passing through the mass flowmeter 16, the wet gas F is fed to a condenser 17 (or gas cooler), in which the wet gas F is cooled to a condenser temperature $T_K$ of for example 5° C. In this cooling, a large part of the water W contained in the wet gas F condenses out and collects as liquid condensate K in a condensate trap 18 of the condenser 17. To a lesser extent, also separated by the separation step proceeding in the condenser 17 are other components D of the wet gas F apart from water W, in particular $CO_2$, which in aqueous solution likewise collects in the condensate trap 18.

The condensate K collecting in the condensate trap 18 forms a separation fluid as defined above. The synthesis gas dried in the separation step is withdrawn from the condenser 17 along the sample gas line 4 and fed to the gas analysis unit 11. This dried synthesis gas, which forms a "residual fluid" as defined above, is referred to hereafter as dry gas T.

The dry gas T passes through a second (Coriolis) mass flowmeter 19, which is arranged within the sample gas line 4 between the condenser 17 and the gas analysis unit 11. The mass flow $m_2$ of the dry gas T is measured directly by this mass flowmeter 19 as a second reference flow rate $M_2$:

$$M_2 := m_2 \qquad \text{Equation 2}$$

The level of the condensate in the condensate trap 18—and as a result of this also the free gas volume in the condenser 17—are kept at least approximately constant by a filling level controller 20 assigned to the condensate trap 18. For this purpose, the filling level controller 20 activates on a clocked basis a withdrawal valve 21, by way of which excess condensate K can be withdrawn from the condensate trap 18 and fed into a condensate line 22.

Optionally, the device 10 includes in the condensate line 22 a further (Coriolis) mass flowmeter 23, by means of which a flow rate $m_3$ of the condensate K can be measured. In alternative embodiments of the device 10, this mass flow $m_3$ may be used instead of the mass flow $m_1$ or $m_2$ as the reference flow rate.

Figure 2:
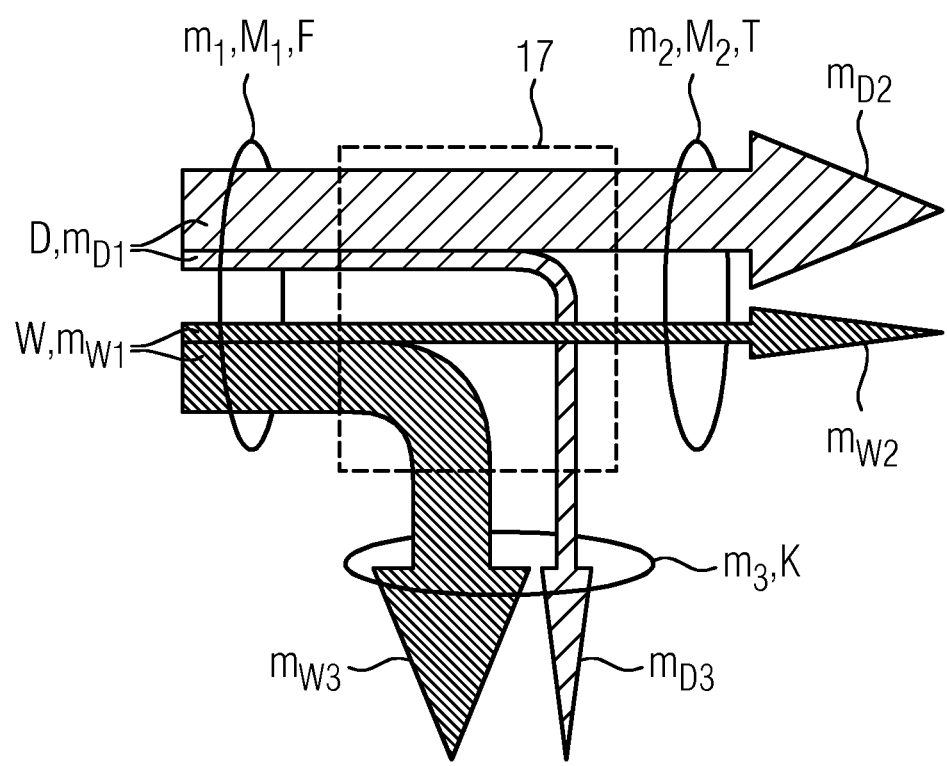
FIG. 2 shows a schematic representation of the mass flows flowing in the sample gas line.

The mass flows $m_1$, $m_2$ and $m_3$ flowing in the sample gas line 4 and the condensate line 18 are represented once again in FIG. 2 in a schematically illustrated manner. It can be seen in particular from this representation that the mass flow $m_1$ of the wet gas F fed to the condenser 17 can be divided into a water mass flow $m_{W1}$ and a mass flow $M_{D1}$ of the other components D. Similarly, the mass flow $m_2$ of the dry gas T can be divided into a water mass flow $m_{W2}$ (which forms the "residual proportion" of the first component as defined above) and a mass flow $M_{D2}$ of the other components D. Finally, the mass flow $m_3$, assigned to the condensate K, can also be divided into a water mass flow $m_{W3}$ and a mass flow $m_{D3}$ of the other components D. The last-mentioned mass flow $m_{D3}$ forms the "extraneous portion" of the other components D in the separation fluid as defined above.

The mass flowmeters 16 and 19 and also—if present—the mass flowmeter 23 are connected in signaling terms to an evaluation unit 24 of the device 10 and continuously feed to this evaluation unit 24 measured values of the reference flow rates $M_1$ and $M_2$ and also optionally of the mass flow $m_3$.

The evaluation unit 24 is preferably a computer, in particular a PC with an evaluation program 25 implemented by software on it. By this evaluation program 25, the mass proportion $x_W$, to be determined according to the method, of the water W contained in the wet gas F is determined on the basis of the reference flow rates $M_1$ and $M_2$ according to the formula $$x_W = \frac{1}{1+\beta} + \left(1 - \frac{1}{1+\beta} - \frac{1}{1+\alpha}\right)\frac{M_2}{M_1} \qquad \text{Equation 3}$$

In Equation 3, the variable $\alpha = \alpha(T_K)$ stands for the mass density proportion of water W in the dry gas T that corresponds to the saturation vapor pressure $p_S$ of water at the condenser temperature $T_K$.

The variable $\beta = \beta(T_K)$ stands for the equilibrium solubility of carbon dioxide and water W at the condenser temperature $T_K$.

The mass density proportion $\alpha$ is preferably derived in approximation from the saturation vapor pressure $p_S(T_K)$ by way of the equation of state ($p \cdot V = v \cdot R_m \cdot T$) applicable to an ideal gas:

$$\alpha(T_K) = \frac{\rho_W(T_K)}{\rho_T(T_K)} = \frac{v_W(T_K) \cdot M_W}{\rho_T(T_K) \cdot V} = \frac{p_S(T_K) \cdot M_W}{\rho_T(T_K) \cdot R_m \cdot T_K} \qquad \text{Equation 4}$$

In Equation 4, the variables $\rho_W = \rho_W(T_K)$ stands for the mass density of the water W contained in the dry gas T at the condenser temperature $T_K$, $\rho_T = \rho_T(T_K)$ stands for the mass density of the dry gas T at the condenser temperature $T_K$, V stands for the gas volume being considered, $v_W = v_W(T_K)$ stands for the amount of substance (mole number) of the water molecules in the gas volume V at the condenser temperature $T_K$, $M_W$ stands for the molar mass of water, and $R_m$ stands for the general gas constant R=8.3144721 J·(mol·K)$^{-1}$.

The mass density $\rho_T$ of the dry gas T is determined by measurement performed by the gas analysis unit 11. Instead of the equation of state for ideal gases, an equation of state applicable to real gases (for example according to Peng-Robinson or Redlich-Kwong-Soave) may also be used for the derivation of the mass density proportion cc from the saturation vapor pressure $p_S(T_K)$.

The evaluation program 25 takes the temperature-dependent values for the variables $\alpha$ and $\beta$ from stored characteristic curves, taking as a basis a value for the condenser temperature $T_K$ determined by measurement. As an alternative to this, the condenser temperature $T_K$ may also be preset within the evaluation program 25 as a fixed value, so that there is no need to measure this temperature.

Equation 3 is obtained computationally on the basis of the fact that the mass flow $m_{W2}$ (residual proportion) of the water W still contained in the dry gas T is proportional to the mass flow $m_{D2}$ of the other components D in the dry gas T by way of the value of the mass density proportion $\alpha$:

$$m_{W2} = \alpha(T_K) \cdot m_{D2} \qquad \text{Equation 5}$$

Furthermore, Equation 3 is based on the assumption that the mass flow $m_{D3}$ of the other components D contained in the condensate K is proportional to the mass flow $m_{W3}$ of the water W contained in the condensate K by way of the carbon dioxide solubility $\beta$:

$$m_{D3} = \beta(T_K) \cdot m_{W3} \qquad \text{Equation 6}$$

Furthermore, Equation 3 is based on the assumption that the mass flows represented in FIG. 2 cancel out to zero:

$$m_1 - m_2 - m_3 = (m_{W1} + m_{D3}) - (m_{W2} + m_{D2}) - (m_{W3} + m_{D3}) = 0 \qquad \text{Equation 7}$$

That this assumption is satisfied with a high degree of accuracy is ensured within the device 10 in particular by the pressure controller 12 and also by the filling level controller 20.

Finally, Equation 2 includes the finding that the mass flow $M_{D3}$ of the further components D that are separated at the same time in the condenser 17 as the "extraneous proportion" consists almost exclusively of carbon dioxide, especially since the other constituents CO, $N_2$ and $H_2$ of the wet gas F have only a much lower solubility in water.

Equation 2 and, building on it, Equation 3 can however easily be extended to embodiments of the invention in which a number of further components D apart from $CO_2$ are present in significant proportions in the extraneous proportion, i.e. the mass flow $m_{D3}$. In this case, the variable β should be calculated as the sum of corresponding solubilities $\beta_i$ (i=1, 2, ..., N) of each component to be taken into account:

$$\beta = \beta_1 + \ldots + \beta_N \quad \text{Equation 8}$$

Correspondingly, Equation 1 can also be extended to a number of components:

$$\alpha = \alpha_1 + \ldots + \alpha_N \quad \text{Equation 9}$$

Furthermore, the device 10 according to the invention—possibly in a modified form—may also be used for determining the mass proportion of a first component from another multi-component fluid. In particular, the proportion of solids in a liquid-solid mixture (for example a sand-water mixture) can be determined by means of a modified embodiment of the invention 10. For this application, instead of the condenser 17, the device 10 particularly comprises a solids separator.

The invention is not restricted to the previously described exemplary embodiments. Rather, further embodiments of the invention can be derived by a person skilled in the art from the foregoing description.

The invention claimed is:

1. A method for determining a mass proportion of a first component (W) of a multi-component fluid (F), comprising
    at least partially separating the first component (W) from the multi-component fluid (F) in a separation step,
    determining at least two reference flow rates ($M_1$, $M_2$), selected from
        a flow rate ($m_1$) of the multi-component fluid (F) fed to the separation step,
        a flow rate ($m_2$) of a residual fluid (T) resulting from the separation of the first component (W), and
        a flow rate ($m_3$) of a separation fluid (K) occurring in the separation step,
    determining the mass proportion ($x_W$) of the first component (W) from the chosen reference flow rates ($M_1$, $M_2$) while taking into account a non-separated residual proportion ($m_{W2}$) of the first component (W) in the residual fluid (T), and
    accounting for an extraneous proportion ($m_{D3}$) of a further component (D) of the multi-component fluid (F) that is separated at the same time in the separation step.

2. The method as claimed in claim 1,
    wherein the reference flow rates ($M_1$, $M_2$) are determined by direct measurement of the mass flow rate ($m_1$, $m_2$) of the multi-component fluid (F), of the residual fluid (T) and of the separation fluid (K).

3. The method as claimed in claim 2,
    wherein the determination of the reference flow rates ($M_1$, $M_2$) takes place in each case by a Coriolis mass flowmeter.

4. The method as claimed in claim 1,
    wherein the pressure (p) of the multi-component fluid (F) fed to the separation step is controlled to a predetermined setpoint value by means of a pressure controller.

5. The method as claimed in claim 4,
    wherein pressure fluctuations of the multi-component fluid (F) fed to the separation step that are caused by the pressure controller are reduced by a damping element arranged downstream of the pressure controller.

6. The method as claimed in claim 1,
    wherein a gas flow is used as the multi-component fluid (F), and in which in the separation step the separation fluid (K) is separated by condensation in a condenser.

7. The method as claimed in claim 6,
    wherein the non-separated residual proportion ($m_{W2}$) of the first component (W) in the residual fluid (T) is determined on the basis of the saturation vapor pressure ($p_S$) at the condenser temperature ($T_K$).

8. The method as claimed in claim 6,
    wherein the extraneous proportion ($m_{D3}$) of the further component (D) in the separation fluid (K) is determined on the basis of the solubility (β) of the further component (D) in the first component (W) at the condenser temperature ($T_K$).

9. The method as claimed in claim 5, wherein the damping element comprises a filter.

* * * * *